United States Patent
Feng et al.

(10) Patent No.: US 11,426,338 B2
(45) Date of Patent: Aug. 30, 2022

(54) NAIL COMPOSITIONS CONTAINING DIISONONYL 1,2-CYCLOHEXANEDICARBOXYLATE

(71) Applicant: L'ORÉAL, Paris (FR)

(72) Inventors: Jianxin Feng, Clark, NJ (US); Ramakrishnan Hariharan, Springfield, NJ (US)

(73) Assignee: L'ORÉAL, Paris (FR)

( * ) Notice: Subject to any disclaimer, the term of this patent is extended or adjusted under 35 U.S.C. 154(b) by 284 days.

(21) Appl. No.: 15/799,919

(22) Filed: Oct. 31, 2017

(65) Prior Publication Data

US 2019/0125642 A1 May 2, 2019

(51) Int. Cl.
*A61K 8/362* (2006.01)
*A61K 8/73* (2006.01)
*A61Q 3/02* (2006.01)
*A61K 8/37* (2006.01)

(52) U.S. Cl.
CPC ............... *A61K 8/362* (2013.01); *A61K 8/37* (2013.01); *A61K 8/731* (2013.01); *A61Q 3/02* (2013.01); *A61K 2800/26* (2013.01); *A61K 2800/31* (2013.01); *A61K 2800/436* (2013.01); *A61K 2800/884* (2013.01)

(58) Field of Classification Search
None
See application file for complete search history.

(56) References Cited

U.S. PATENT DOCUMENTS

| 2003/0012750 | A1* | 1/2003 | Socci ................. A61K 8/0204 424/61 |
| 2007/0003583 | A1 | 1/2007 | Storzum et al. |
| 2015/0210827 | A1* | 7/2015 | Yontz ................. C08K 5/1565 521/90 |
| 2017/0056313 | A1 | 3/2017 | Valia et al. |

FOREIGN PATENT DOCUMENTS

| CN | 102512331 | 6/2012 |
| EP | 1 475 071 | 11/2004 |

* cited by examiner

*Primary Examiner* — Nicole P Babson
(74) *Attorney, Agent, or Firm* — Oblon, McClelland, Maier & Neustadt, L.L.P.

(57) ABSTRACT

The invention relates to nail compositions including diisononyl 1,2-cyclohexanedicarboxylate, as well as to methods, kits and nail composition sets related to such compositions.

10 Claims, No Drawings

NAIL COMPOSITIONS CONTAINING DIISONONYL 1,2-CYCLOHEXANEDICARBOXYLATE

FIELD OF THE INVENTION

The present invention relates to nail compositions comprising diisononyl 1,2-cyclohexanedicarboxylate, as well as to methods of improving hardness and shine properties of nail compositions by including diisononyl 1,2-cyclohexanedicarboxylate in the nail compositions.

DISCUSSION OF THE BACKGROUND

Diisononyl 1,2-cyclohexanedicarboxylate is marketed by BASF under the brand name of Hexamoll® Dinch® and has been approved for many applications in medical devices, food contact packaging and toys. It is disclosed in European Patent 1475071.

Diisononyl 1,2-cyclohexanedicarboxylate has a structure which differs from typical nail polish plasticizers such as phosphates, phthalates, citrates and camphor.

US 2017/0056313 disclose UV-gel nail coatings assertedly having enhanced adhesion.

CN 102512331 appears to disclose a multi-component nail polish that changes with temperature, with one component possibly having an extremely small amount of cyclohexane diisononyl ester.

There remains a need for new ways to improve hardness and shine properties in solvent-based nail compositions, particularly nail compositions containing a cellulose compound like nitrocellulose.

SUMMARY OF THE INVENTION

The present invention relates to a nail composition comprising at least 5% diisononyl 1,2-cyclohexanedicarboxylate by weight with respect to the total weight of the composition. Preferably, the nail composition further comprises nitrocellulose.

The present invention also relates to a nail composition comprising at least one coloring agent and at least 5% diisononyl 1,2-cyclohexanedicarboxylate by weight with respect to the total weight of the composition. Preferably, the nail composition further comprises nitrocellulose.

The present invention also relates to a nail composition set comprising at least one color coat comprising at least one coloring agent and at least one topcoat comprising at least 5% diisononyl 1,2-cyclohexanedicarboxylate by weight with respect to the total weight of the topcoat. Preferably, the color coat and/or topcoat further comprises nitrocellulose.

The present invention also relates to a kit comprising at least one color coat composition comprising at least one coloring agent and at least one topcoat comprising at least 5% diisononyl 1,2-cyclohexanedicarboxylate by weight with respect to the total weight of the topcoat. Preferably, the color coat and/or topcoat further comprises nitrocellulose.

The present invention also relates to a nail composition set comprising at least one color coat comprising at least one coloring agent and at least one basecoat comprising at least 5% diisononyl 1,2-cyclohexanedicarboxylate by weight with respect to the total weight of the basecoat. Preferably, the color coat and/or basecoat further comprises nitrocellulose.

The present invention also relates to a kit comprising at least one color coat composition comprising at least one coloring agent and at least one basecoat comprising at least 5% diisononyl 1,2-cyclohexanedicarboxylate by weight with respect to the total weight of the basecoat. Preferably, the color coat and/or basecoat further comprises nitrocellulose.

The present invention also relates to methods of improving shine and/or hardness properties of a nail composition comprising adding at least 5% diisononyl 1,2-cyclohexanedicarboxylate by weight with respect to the total weight of the composition to the nail composition during preparation of the nail composition. Preferably, the nail composition further comprises nitrocellulose.

The present invention further relates to methods for making up and/or protecting nails comprising applying to the nails a nail composition comprising at least 5% diisononyl 1,2-cyclohexanedicarboxylate by weight with respect to the total weight of the composition. Preferably, the nail composition further comprises nitrocellulose.

The present invention further relates to methods for making up and/or protecting nails comprising applying to the nails (1) at least one color coat comprising at least one coloring agent, and (2) at least one topcoat comprising at least 5% diisononyl 1,2-cyclohexanedicarboxylate by weight with respect to the total weight of the topcoat. Preferably, the color coat and/or topcoat further comprises nitrocellulose.

The present invention further relates to methods for making up and/or protecting nails comprising applying to the nails (1) at least one basecoat comprising at least 5% diisononyl 1,2-cyclohexanedicarboxylate by weight with respect to the total weight of the basecoat; and (2) at least one color coat comprising at least one coloring agent. Preferably, the color coat and/or basecoat further comprises nitrocellulose.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Adhesion" as used herein, refers to chemical or physical bonding between a coating and a substrate. Good adhesion between nail polish and nail surface should translate to good wear properties on consumers. Adhesion properties can be quantified by in-vitro method such as a cross-cut adhesion test. In the test, a lattice pattern is cut into the coating and penetrates through to the substrate. A pressure sensitive tape is applied to the sample and then pulled off. The adhesion property can be quantified by the area of the coating remaining after peeling. For example, if the whole film remains after peeling, it indicates excellent adhesion. If most of the film gets peeled off, it indicates poor adhesion. The cross-cut test is an industrial standard test for testing adhesion for coatings. (Reference #ISO/DIN 2409, ASTM D3359).

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Nail" as used herein includes fingernails as well as toenails.

"Volatile", as used herein, means having a flash point of less than about 100° C.

"Non-volatile", as used herein, means having a flash point of greater than about 100° C.

"Shine" or "gloss" as used herein, refers to surface shininess. Gloss meters are commonly used in the nail composition art, and can measure the amount of light reflected from the surface or film of interest. Gloss may be quantified, for example, as a % reflectance at 20° or at 60° angles. Shine/gloss can be determined according to the following procedure: A thin layer of a tested composition can be applied on a drawdown chart (Byko-opacity chart 5C, 7.6.times.10.25 inch). Gloss of the coating can be measured at 20° or 60° by using the Micro-TRI-Gloss meter, available from BYK-Gardner and expressed by gloss units (GU).

"Shine enhancing agent" or "shine increasing agent" refers to an agent which increases shine or gloss in a composition.

"Hardness" as used herein, refers to how resistant a material is to various kinds of permanent shape change when a force is applied. The force can be measured and quantified as described in this application.

"Persoz hardness" can be determined by applying a thin layer (coating) of a tested composition on a metal plate and measuring hardness using a Pendulum Hardness Tester (Persoz pendulum) equipped with a temperature and humidity control chamber (30±2° C., 70±2% RH) according to ASTM method D4366-95. The higher the Persoz number, the harder the layer (coating) is For example, Persoz hardness may be determined using a Persoz pendulum at a defined temperature, e.g. 30° C., and at a defined humidity rate, e.g. at 50% relative humidity (RH). The adhesive side of the article is applied to a glass plate and is then dried at 30° C. for a desired period such as 23 hours (h) or seven days, then for one additional hour in the environment of the pendulum. The Persoz pendulum is then positioned above the plate. The time required by the Persoz pendulum to oscillate from an amplitude of 12° to an amplitude of 4° is then determined. A plurality of measurements, e.g. ten measurements, can be taken so as to establish an average of the calculated results.

The compositions, coats and methods of the present invention can comprise, consist of, or consist essentially of the essential elements and limitations of the invention described herein, as well as any additional or optional ingredients, components, or limitations described herein or otherwise useful. For example, the plasticizing component of the compositions and coats of the present invention can "consist essentially of" or "consist of" diisononyl 1,2-cyclohexanedicarboxylate.

In this regard, the "plasticizing component" comprises diisononyl 1,2-cyclohexanedicarboxylate and optionally may contain one or more additional plasticizing agents. Preferably, the plasticizing component contains a majority (greater than 50% by weight) of diisononyl 1,2-cyclohexanedicarboxylate, preferably greater than 60% by weight, preferably greater than 70% by weight, preferably greater than 80% by weight, preferably greater than 90% by weight, and may contain up to 100% by weight of diisononyl 1,2-cyclohexanedicarboxylate, all percentages being based on weight of diisononyl 1,2-cyclohexanedicarboxylate with respect to the total weight of the plasticizing component. All ranges and subranges within the percentages set forth above are included herein such as, for example, 10%-100% by weight, 25%-90% by weight, 50%-85% by weight, etc.

For purposes of the compositions, components and methods of the present invention where the invention "consists essentially of" the identified ingredients and/or process steps, the two "basic and novel properties" of such compositions, components and/or methods are "increasing shine" and "decreasing hardness."

Nail Composition

According to the present invention, a nail composition comprising at least 5% diisononyl 1,2-cyclohexanedicarboxylate by weight with respect to the total weight of the composition is provided. Preferably, the nail composition comprises at least 6% diisononyl 1,2-cyclohexanedicarboxylate by weight with respect to the total weight of the composition, preferably at least 7% diisononyl 1,2-cyclohexanedicarboxylate by weight with respect to the total weight of the composition, preferably at least 8% diisononyl 1,2-cyclohexanedicarboxylate by weight with respect to the total weight of the composition, and preferably at least 9% diisononyl 1,2-cyclohexanedicarboxylate by weight with respect to the total weight of the composition, up to 50% diisononyl 1,2-cyclohexanedicarboxylate by weight with respect to the total weight of the composition. All ranges and subranges within the percentages set forth above are included herein such as, for example, 5%-50%, 6%-40%, 7%-30%, 8%-50%, 10%-33%, etc., by weight with respect to the total weight of the composition.

Other Ingredients

According to the present invention, a nail composition comprising at least one other ingredient typically found in nail compositions is provided. One of ordinary skill in the art would readily understand the types of ingredients typically found in nail compositions. A non-exhaustive list of such ingredients includes, but is not limited to, cellulose compounds, plasticizing agents, coalescing agents, and coloring agents.

Suitable cellulose compounds include, but are not limited to, cellulose polymers, such as, for example, hydroxyethyl cellulose, hydroxypropylcellulose, methylcellulose, ethylhydroxyethylcellulose and nitrocellulose.

According to preferred embodiments, the at least one cellulose compound, if present, is present in the compositions of the present invention in an amount of active material ranging from about 0.01 to about 30% by weight, more preferably from about 0.1 to about 20% by weight, and most preferably from about 1 to about 10% by weight, based on the total weight of the composition, including all ranges and subranges within these ranges.

According to preferred embodiments, the at least one cellulose compound and the diisononyl 1,2-cyclohexanedicarboxylate are present in a weight ratio of 7:1 to 1:7, preferably 5:1 to 1:5, preferably 3:1 to 1:3, preferably about 2:1 to about 1:2, including all ranges and subranges therebetween such as, for example, 7:1 to 2:1, 5:1 to 1:3, 3:1 to 1:2.5, etc. In embodiments of the present invention in which a nail composition comprises both the cellulose compound and the diisononyl 1,2-cyclohexanedicarboxylate, the above weight ratios are present in the nail composition. In embodiments of the present invention in which the cellulose compound and the diisononyl 1,2-cyclohexanedicarboxylate are present in different compositions or coats of the present invention, the above weight ratios can be satisfied by the presence of the ingredients in their respective compositions or coats.

According to preferred embodiments, the cellulose compound is nitrocellulose. Also according to preferred embodiments, nitrocellulose is present in the compositions of the present invention in the amounts and ratios set forth in the preceding two paragraphs.

The plasticizing component of the compositions of the present invention may optionally contain one or more plasticizers in addition to diisononyl 1,2-cyclohexanedicarboxylate. Plasticizers (plasticizing agents) are additives used to optimize the mechanical properties of the films. They tend to reduce the Glass Transition Temperature (Tg) and increase the softness and flexibility of the films. Preferably, the plasticizer has a distribution coefficient D of less than or equal to 0.1. The distribution coefficient can be determined in accordance with the teaching of "A method to predict the distribution coefficient of coalescing agents between latex particles and the water phase," *Progress in Organic Coatings*, vol. 30, 1997, pp. 173-177, the disclosure of which is specifically incorporated by reference herein.

Preferably, the plasticizer has a boiling point measured at ambient pressure of less than or equal to 285° C., preferably less than or equal to 270° C., and preferably less than or equal to 250° C. In the present specification, the boiling point values are to be considered accurate to ±2° C. owing to the uncertainties of boiling point measurement.

Any plasticizing agent typically found in nail polish compositions can be used. Examples of suitable plasticizers include, but are not limited to, glycols and their ester derivatives, esters of acids, in particular carboxylic acids, such as citrates, adipates, carbonates, tartrates, phosphates or sebacates, oxyethylenated derivatives, such as oxyethylenated oils, and their mixtures. For example, suitable plasticizing agents include, but are not limited to, diisobutyl adipate, the ester of teributyl acid and 2,2,4-trimethylpentane-1,3-diol, diethyl adipate, diethyl phthalate, dibutyl phthalate, dioctyl phthalate, butyl 2-ethylhexyl phthalate, dimethyl sebacate, dibutyl sebacate, ethyl stearate, 2-ethylhexyl palmitate, dipropylene glycol n-butyl ether, tributyl phosphate, tributoxyethyl phosphate, tricresyl phosphate, triphenyl phosphate, glycerol triacetate, butyl stearate, butyl glycolate, benzyl benzoate, butyl acetyltricinoleate, glyceryl acetyltricinoleate, dibutyl phthalate, diisobutyl phthalate, dioctyl phthalate, dimethoxyethyl phthalate, diamyl phthalate, triethyl citrate, tributyl citrate, tributyl acetylcitrate, tri(2-ethylhexyl) acetylcitrate, dibutyl tartrate, camphor, and mixtures thereof.

In accordance with preferred embodiments, the plasticizing component is present in the compositions of the present invention in an amount of from 5% to 50% by weight, preferably from 6% to 40% by weight, preferably from 7% to 30% by weight, of the total weight of the composition, including all ranges and subranges therebetween.

According to preferred embodiments, the compositions of the present invention are substantially free of phthalates (i.e., contain less than about 0.5% phthalates). In other embodiments, the compositions are free of phthalates (i.e., contain less than about 0.25% phthalates) or devoid of phthalates (i.e., contain less than about 0.1% phthalates).

Coalescents (coalescing agents) are additives used assist the film formation process of certain film forming agents (e.g., latex). Preferably, the coalescent agent has a distribution coefficient D' of greater than or equal to 0.5, measured in accordance with the above-referenced "A method to predict the distribution coefficient of coalescing agents between latex particles and the water phase," *Progress in Organic Coatings*, vol. 30, 1997, pp. 173-177. Preferably, the coalescent agent has a boiling point measured at ambient pressure ranging from 90° C. to 180° C., preferably from 150° C. to 180° C.

Any coalescent agent typically found in nail polish compositions can be used. Examples of suitable plasticizers include, but are not limited to, propylene glycol n-butyl ether, dipropylene glycol dimethyl ether, propylene glycol methyl ether acetate, propylene glycol propyl ether, methyl lactate, ethyl lactate, isopropyl lactate, and mixtures thereof.

In accordance with preferred embodiments, the coalescent agent, if present, is preferably present in the primer composition in an amount of from 0.1% to 25% by weight, preferably from 1% to 15% by weight, preferably from 3 to 10% by weight, of the total weight of the composition, including all ranges and subranges therebetween.

Suitable colorants (coloring agents) include any colorant typically found in nail compositions. Suitable colorants include, but are not limited to, lipophilic dyes, pigments and pearlescent agents, and their mixtures.

Suitable examples of fat-soluble dyes are, for example, Sudan red, DC Red 17, DC Green 6, β-carotene, soybean oil, Sudan brown, DC Yellow 11, DC Violet 2, DC Orange 5 and quinoline yellow.

Suitable pigments can be white or colored, inorganic and/or organic and coated or uncoated. Mention may be made, for example, of inorganic pigments such as titanium dioxide, optionally surface treated, zirconium or cerium oxides and iron or chromium oxides, manganese violet, ultramarine blue, chromium hydrate and ferric blue. Mention may also be made, among organic pigments, of carbon black, pigments of D & C type and lakes based on cochineal carmine or on barium, strontium, calcium or aluminum, such as D&C Red No. 10, 11, 12, and 13, D&C Red No. 7, D&C Red No. 5 and 6, and D&D Red No. 34, as well as lakes such as D&C Yellow Lake No. 5 and D&C Red Lake No. 2.

Suitable pearlescent pigments can be chosen from, for example, white pearlescent pigments, such as mica covered with titanium oxide or with bismuth oxychloride, colored pearlescent pigments, such as titanium oxide-coated mica with iron oxides, titanium oxide-coated mica with in particular ferric blue or chromium oxide, or titanium oxide-coated mica with an organic pigment of the abovementioned type, and pearlescent pigments based on bismuth oxychloride.

In accordance with preferred embodiments of nail compositions providing color to a nail, the colorant is preferably present in an amount sufficient to provide color to the nail, preferably in an amount of from about 0.1% to about 20% by weight, preferably from about 0.25% to about 15% by weight, and preferably from about 0.5 to about 10% by weight, of the total weight of the composition, including all ranges and subranges therebetween.

According to preferred embodiments, compositions of the present invention possess high shine (gloss) and/or softness properties (high softness being related to low hardness). High softness/low hardness helps to minimize adverse effects of a hard nail composition such as chipping.

According to preferred embodiments, compositions of the present invention possess shine (gloss) greater than about 55

GU (Gloss Units) measured at 20° angle, preferably greater than about 60 GU, preferably greater than about 65 GU.

According to preferred embodiments, compositions of the present invention possess shine (gloss) greater than about 70 GU (Gloss Units) measured at 60° angle, preferably greater than about 75 GU, preferably greater than about 80 GU.

According to preferred embodiments, compositions of the present invention possess softness properties such that the compositions have a Persoz hardness of less than 100, preferably less than 90, and preferably less than 80 and preferably greater than 20, preferably greater than 30 and preferably greater than 40 for color coat compositions.

According to preferred embodiments, compositions of the present invention possess softness properties such that the compositions have a Persoz hardness of less than 175, preferably less than 160, and preferably less than 150 and preferably greater than 50, preferably greater than 60 and preferably greater than 70 for topcoat compositions.

According to preferred embodiments, compositions of the present invention possess both high shine (gloss) and softness (to minimize adverse effects of a hard nail composition such as chipping) properties as described above.

According to preferred embodiments, the nail composition has a smooth appearance (that is, visual ridges do not appear) on the nail.

Nail Composition Set

According to the present invention, nail composition sets comprising (1) at least one color coat comprising at least one coloring agent and (2) at least one basecoat comprising diisononyl 1,2-cyclohexanedicarboxylate and/or at least one topcoat comprising diisononyl 1,2-cyclohexanedicarboxylate are provided.

According to preferred embodiments, the basecoat and/or topcoat of the nail composition set has a smooth appearance (that is, visual ridges do not appear) on the nail.

For example, a nail composition set comprising at least one basecoat, at least one color coat and at least one topcoat are provided. However, the basecoat or topcoat is optional. Thus, nail composition sets comprising at least one color coat and at least one top coat, as well as nail composition sets comprising at least one basecoat and at least one color coat are provided by the present invention.

It should be understood that each coat or layer in the nail composition set, itself, can comprise one or more layers of each composition. Thus, the at least one basecoat can comprise one or more basecoat layers; the at least one color coat can comprise one or more color coat layers; and the at least one topcoat can comprise one or more topcoat layers. Preferably, each basecoat, color coat and topcoat contains three or fewer layers or compositions, more preferably two or fewer layers or compositions, and most preferably a single layer or composition.

According to the present invention, the basecoat, color coat and topcoat of the nail composition set can be any suitable solvent-based composition for application to nails. For example, the basecoat(s) can be an adhesive layer or an undercoat layer; and the topcoat(s) can be a protective layer.

Examples of suitable conventional solvent-based compositions can be found, for example, in U.S. Pat. Nos. 7,455,831, 7,025,953, 6,555,096, 6,372,201, 6,333,025, and 6,254,878, the entire contents of all of which are hereby incorporated by reference in their entireties.

During application of the nail composition set, the basecoat (if used) is applied to the nail. The color coat is applied to the basecoat (if used); if basecoat is not used, the color coat is applied to the nail. Then, if used, the topcoat is applied to the color coat. In this manner, a nail composition set comprising a basecoat (optional), a color coat and a topcoat (optional) can be prepared on a nail.

Auxiliaries/Additives

The compositions discussed above may additionally comprise an additive or auxiliary commonly used in cosmetic compositions and known to a person skilled in the art as being capable of being incorporated into a nail polish or varnish composition. Such additives or auxiliaries may be chosen from solvents, thickeners, coalescents, preservatives, fragrances, oils, waxes, surfactants, antioxidants, agents for combating free radicals, spreading agents, wetting agents, dispersing agents, antifoaming agents, neutralizing agents, stabilizing agents, active principles chosen from essential oils, UV screening agents, sunscreens, moisturizing agents, vitamins, proteins, ceramides, plant extracts, fibers, and the like, and their mixtures.

A person skilled in the art will take care to select the optional additional additives and/or the amount thereof such that the advantageous properties of the compositions according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the compositions of the invention should be cosmetically or dermatologically acceptable, i.e., they should contain a non-toxic physiologically acceptable. The compositions may be in any galenic form normally employed in the cosmetic and dermatological fields which is suitable for topical administration onto nails.

According to preferred embodiments, compositions of the invention comprise at least one organic solvent. Suitable examples of solvents, include, but are not limited to, ketones which are liquid at room temperature such as, for example, methyl ethyl ketone, methyl isobutyl ketone, diisobutyl ketone, isophorone, cyclohexanone, and acetone; alcohols which are liquid at room temperature, such as ethanol, isopropanol, n-propanol, n-butanol, diacetone alcohol, 2-butoxyethanol, and cyclohexanol; glycols which are liquid at room temperature, such as ethylene glycol, propylene glycol, pentylene glycol, and glycerol; propylene glycol ethers which are liquid at room temperature, such as propylene glycol monomethyl ether, propylene glycol monomethyl ether acetate, and dipropylene glycol mono-n-butyl ether; short-chain esters (having from 3 to 8 carbon atoms in total) such as ethyl acetate, methyl acetate, propyl acetate, n-butyl acetate, and isopentyl acetate; ethers which are liquid at room temperature, such as diethyl ether, dimethyl ether, and dichlorodiethyl ether; alkanes which are liquid at room temperature such as decane, heptane, dodecane, isododecane, and cyclohexane; aromatic cyclic compounds which are liquid at room temperature, such as toluene and xylene; and aldehydes which are liquid at room temperature, such as benzaldehyde and acetaldehyde. If present, the organic solvent preferably comprises from about 10% to about 95% by weight, preferably from about 30% to about 90% by weight, and preferably from about 50% to about 85% by weight, relative to the total weight of the composition.

According to preferred embodiments, the compositions of the present invention are substantially free of water (i.e., contain less than about 1% water). In other embodiments, the compositions are devoid of water (i.e., contain less than about 0.1% water).

According to preferred embodiments of the present invention, methods for making up and/or protecting nails comprising applying to the nails (1) at least one basecoat comprising diisononyl 1,2-cyclohexanedicarboxylate; and (2) at least one color coat comprising at least one coloring agent are provided.

According to preferred embodiments of the present invention, methods for making up and/or protecting nails comprising applying to the nails (1) at least one color coat comprising at least one coloring agent, and (2) at least one topcoat comprising diisononyl 1,2-cyclohexanedicarboxylate are provided.

"Making up" as used herein means to provide decoration (for example, color) to the nail. "Protecting" as used herein means to inhibit damage to the nail (for example, chipping) by providing a protective layer on the nail.

In accordance with preferred embodiments of the preceding methods, at least one color coat is applied topically to the nails of a person in need of (desirous) the desired making up or protection in an amount sufficient to achieve the desired result. The coats may be applied to the desired area as needed.

According to preferred embodiments of the present invention, a kit comprising (1) at least one basecoat composition comprising diisononyl 1,2-cyclohexanedicarboxylate; and (2) at least one color coat composition comprising at least one coloring agent is provided.

According to preferred embodiments of the present invention, a kit comprising (1) at least one color coat composition comprising at least one coloring agent, and (2) at least one topcoat composition comprising diisononyl 1,2-cyclohexanedicarboxylate is provided.

The compositions according to the invention can be manufactured by known processes used generally in the cosmetics or dermatological field.

According to preferred embodiments of the present invention, methods of improving shine and/or hardness properties of a composition of the present invention comprising adding at least 5% diisononyl 1,2-cyclohexanedicarboxylate by weight with respect to the total weight of the composition to the composition during preparation of the composition are provided. Preferably, the composition further comprises nitrocellulose.

Preferably, sufficient diisononyl 1,2-cyclohexanedicarboxylate is added to the composition to provide the composition with gloss properties, measured at 20°, of greater than or equal to 55 GU, preferably greater than or equal to 60 GU, and preferably greater than or equal to 65 GU.

Preferably, sufficient diisononyl 1,2-cyclohexanedicarboxylate is added to the composition to provide the composition with gloss properties, measured at 60°, of greater than or equal to 70 GU, preferably greater than or equal to 75 GU, and preferably greater than or equal to 80 GU.

Preferably, sufficient diisononyl 1,2-cyclohexanedicarboxylate is added to the lower the Persoz hardness of the composition to less than 100, preferably less than 90, and preferably less than 80 and preferably greater than 20, preferably greater than 30 and preferably greater than 40 for color coat compositions.

Preferably, sufficient diisononyl 1,2-cyclohexanedicarboxylate is added to the lower the Persoz hardness of the composition to less than 175, preferably less than 160, and preferably less than 150 and preferably greater than 50, preferably greater than 60 and preferably greater than 70 for topcoat compositions.

Preferably, sufficient diisononyl 1,2-cyclohexanedicarboxylate is added to the composition to provide the composition with gloss properties, measured at 20° or 60°, which is more than 10% greater than the gloss properties of the composition without the diisononyl 1,2-cyclohexanedicarboxylate, preferably more than 15% greater (so, for example, a nail composition without diisononyl 1,2-cyclohexanedicarboxylate having an gloss of 50 which has its gloss increased to 55 after addition of diisononyl 1,2-cyclohexanedicarboxylate corresponds to a gloss value which is 10% greater).

Preferably, sufficient diisononyl 1,2-cyclohexanedicarboxylate is added to the composition to provide the composition with Persoz hardness which is more than 40% lower than the Persoz hardness of the composition without the diisononyl 1,2-cyclohexanedicarboxylate, preferably more than 50% lower, and preferably more than 60% lower (so, for example, a nail composition without diisononyl 1,2-cyclohexanedicarboxylate having a Persoz hardness of 250 which has its Persoz hardness decreased to 125 after addition of diisononyl 1,2-cyclohexanedicarboxylate corresponds to a Persoz hardness value which is 50% lower).

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example 1: Color Coat Containing Coloring Agent and Diisononyl 1,2-Cyclohexanedicarboxylate

| Ingredient | Amount |
| --- | --- |
| Citric Acid | 0.03 |
| Tributyl Citrate | 0.67 |
| Colorant | 1.6 |
| Filler (Hectorite) | 0.8 |
| Film Former | 13.7 |
| Nitrocellulose (and) Isopropyl Alcohol | 14 |
| Diisononyl 1,2-cyclohexanedicarboxylate | 6 |
| Silicone Oil | 0.1 |
| Solvent | 62.5 |
| UV Filter | 0.55 |

Example 2: Topcoat Containing Coloring Agent and Diisononyl 1,2-Cyclohexanedicarboxylate

| Ingredient | Amount |
|---|---|
| Film Former | 8.9 |
| Nitrocellulose (and) Isopropyl Alcohol | 13.6 |
| Diisononyl 1,2-cyclohexanedicarboxylate | 8 |
| Solvent | 69.5 |

Example 3: Comparative Testing

The compositions from Examples 1 and 2 were subjected to gloss testing and Persoz hardness testing.

Gloss of the compositions was determined as follows: Films were drawn down onto Laneta Form 5C—Opacity cards and allowed to dry. Gloss measurements were made using a BYK micro-TRI-gloss meter at both the 20° and the 60° reflectance angle.

Persoz hardness values were determined in accordance with the method described above.

The results are reproduced in the Table below.

| Property | Example 1 | Example 2 |
|---|---|---|
| Gloss (20°) | 54.7 | 81.8 |
| Gloss (60°) | 83.6 | 89.5 |
| Persoz Hardness (1 day) | 47 (24 hours) | 129 (20 hours) |
| Persoz Hardness (5 days) | 56 | ND |

Example 4: Comparative Testing

The following nitrocellulose-containing base composition was prepared:

| Ingredient | Amount |
|---|---|
| Ethyl Acetate | 60 |
| Isopropyl Alcohol | 12 |
| Nitrocellulose | 28 |
| Total | 100 |

The gloss and Persoz hardness of the base composition was determined. Also, different plasticizers (identified in the tables below) were included in the base composition at 3%, 5% and 7% levels, and the gloss and Persoz hardness properties of each composition was determined.

Gloss (at both the 20° and the 60° reflectance angle) and Persoz hardness values were determined in accordance with the methods described above.

The results are reflected below.

Persoz hardness:

| Plasticizers | 3% | 5% | 7% |
|---|---|---|---|
| | Persoz Hardness (Day 1) | | |
| dipropylene glycol dibenzoate | 283 | 221 | 138 |
| Acetyl tributyl citrate | 266 | 259 | 168 |
| Hexamoll Dinch | 295 | 198 | 118 |
| Becksol 1351 | 213 | 174 | 137 |
| sucrose acetate isobutyrate | 317 | 329 | 325 |
| trimethyl pentanyl diisobutyrate | 299 | 251 | 163 |
| tributyl citrate | 298 | 270 | 147 |
| Octyldodecanol | 169 | 134 | 103 |
| Base Composition | N.D. | N.D. | 246 |
| | Persoz Hardness (Day 7) | | |
| dipropylene glycol dibenzoate | 300 | 755 | 170 |
| Acetyl tributyl citrate | 285 | 255 | 160 |
| Hexamoll Dinch | 298 | 221 | 120 |
| Becksol 1351 | 283 | 218 | 143 |
| sucrose acetate isobutyrate | 321 | 322 | 316 |
| trimethyl pentanyl diisobutyrate | 296 | 259 | 247 |
| tributyl citrate | 298 | 244 | 136 |
| Octyldodecanol | 157 | 130 | 119 |
| Base Composition | N.D. | N.D. | 313 |

Shine

| Plasticizers | 3% | 5% | 7% |
|---|---|---|---|
| | Shine 20° | | |
| dipropylene glycol dibenzoate | 73.6 | 72.8 | 73 |
| Acetyl tributyl citrate | 65 | 63.7 | 65.4 |
| Hexamoll Dinch | 68.3 | 68.7 | 71.9 |
| Becksol 1351 | 69 | 71.2 | 70.5 |
| sucrose acetate isobutyrate | 63.9 | 65.6 | 67.6 |
| Adipic acid neopentyl glycol trimellitic anhydide copolymer | 70.1 | 70.4 | 72.4 |
| Triacetin | 68.5 | 69.9 | 68 |
| trimethyl pentanyl diisobutyrate | 61.4 | 64.3 | 70 |
| tributyl citrate | 61.8 | 65.4 | 64.3 |
| Octyldodecanol | 63.5 | 55.1 | 54.5 |
| Base Composition | N.D. | N.D. | 62.2 |
| | Shine 60° | | |
| dipropylene glycol dibenzoate | 94.9 | 95.4 | 95.9 |
| Acetyl tributyl citrate | 89.6 | 87.8 | 88.6 |
| Hexamoll Dinch | 89.9 | 89.2 | 89.1 |
| Becksol 1351 | 92.5 | 92.5 | 92.5 |
| sucrose acetate isobutyrate | 90.1 | 89.1 | 88.4 |
| Adipic acid neopentyl glycol trimellitic anhydide copolymer | 92.3 | 91.9 | 92.9 |
| Triacetin | 89.8 | 89.5 | 88.6 |
| trimethyl pentanyl diisobutyrate | 89 | 88.4 | 88.5 |
| tributyl citrate | 89.7 | 89.1 | 88.5 |
| Octyldodecanol | 89.8 | 82.4 | 84.7 |
| Base Composition | N.D. | N.D. | 92.6 |

What is claimed is:

1. A nail composition, comprising:
   a solvent;
   a cellulose polymer; and
   a plasticizing component consisting of diisononyl 1,2-cyclohexanedicarboxylate and optionally one or more additional plasticizing agents selected from the group consisting of diisobutyl adipate, the ester of teributyl acid and 2,2,4-trimethylpentane-1,3-diol, diethyl adipate, dimethyl sebacate, dibutyl sebacate, ethyl stearate, 2-ethylhexyl palmitate, dipropylene glycol n-butyl ether, tributyl phosphate, tributoxyethyl phosphate, tricresyl phosphate, triphenyl phosphate, glycerol triacetate, butyl stearate, butyl glycolate, benzyl benzoate, butyl acetylricinoleate, glyceryl acetylricinoleate, triethyl citrate, tributyl citrate, tributyl acetylcitrate, tri(2-ethylhexyl) acetylcitrate, dibutyl tartrate, camphor and mixtures thereof;

wherein the content of the diisononyl 1,2-cyclohexanedicarboxylate is at least 6% by weight with respect to the total weight of the composition, and wherein a Persoz hardness of the composition is more than 50% lower than the Persoz hardness of the composition without the diisononyl 1,2-cyclohexanedicarboxylate.

2. The nail composition of claim 1, wherein the diisononyl 1,2-cyclohexanedicarboxylate and the cellulose polymer are present in a weight ratio of 7:1 to 1:7.

3. The nail composition of claim 2, wherein the cellulose polymer is nitrocellulose.

4. The nail composition of claim 2, wherein the composition has gloss properties, measured at 20°, of greater than about 55 GU.

5. The nail composition of claim 2, wherein the composition has gloss properties, measured at 60°, of greater than about 70 GU.

6. The nail composition of claim 2, further comprising at least one coloring agent.

7. The nail composition of claim 2, wherein the composition is a topcoat.

8. The nail composition of claim 2, which is substantially free of phthalates.

9. The nail composition of claim 2, which is substantially free of water.

10. A nail composition set comprising (a) at least one color coat comprising at least one coloring agent; and (b) at least one basecoat nail composition according to claim 1 and/or at least one topcoat nail composition according to claim 1, wherein the nail composition set has at least one of the following properties:
  a. the nail composition set has gloss properties, measured at 20°; of greater than about 55 GU; or
  b. the nail composition set has gloss properties, measured at 60°, of greater than about 70 GU.

* * * * *